US011851385B2

(12) United States Patent
Cerasoli et al.

(10) Patent No.: US 11,851,385 B2
(45) Date of Patent: Dec. 26, 2023

(54) PROCESS FOR PRODUCING DIENES

(71) Applicant: VERSALIS S.P.A., San Donato Milanese (IT)

(72) Inventors: Talisa Cerasoli, Novara (IT); Stefano Ramello, Novara (IT); Monica Vittoria Pastori, Novara (IT)

(73) Assignee: VERSALIS S.P.A., San Donato Milanese (IT)

( * ) Notice: Subject to any disclaimer, the term of this patent is extended or adjusted under 35 U.S.C. 154(b) by 0 days.

(21) Appl. No.: 17/787,754

(22) PCT Filed: Dec. 18, 2020

(86) PCT No.: PCT/IB2020/062177
§ 371 (c)(1),
(2) Date: Jun. 21, 2022

(87) PCT Pub. No.: WO2021/124242
PCT Pub. Date: Jun. 24, 2021

(65) Prior Publication Data
US 2023/0085074 A1 Mar. 16, 2023

(30) Foreign Application Priority Data
Dec. 20, 2019 (IT) .................. 102019000025000

(51) Int. Cl.
*C07C 1/24* (2006.01)

(52) U.S. Cl.
CPC ............ *C07C 1/24* (2013.01); *C07C 2521/04* (2013.01); *C07C 2521/08* (2013.01)

(58) Field of Classification Search
CPC ........... C07C 29/60; C07C 1/24; C07C 33/03; C07C 33/025; C07C 11/167; B01J 5/1057; B01J 35/0006; B01J 29/084; B01J 35/1066; B01J 29/08; B01J 29/7034; B01J 23/10; B01J 35/1057
See application file for complete search history.

(56) References Cited

U.S. PATENT DOCUMENTS

| | | |
|---|---|---|
| 2,237,866 A | 4/1941 | Guinot et al. |
| 2,310,809 A | 2/1943 | Reppe et al. |
| 2,426,678 A | 9/1947 | Greenberg |
| 3,689,477 A | 9/1972 | Fujita et al. |
| 3,714,285 A | 1/1973 | Mueller et al. |
| 3,974,099 A | 8/1976 | Lussier et al. |
| 4,175,118 A | 11/1979 | Wassermann et al. |
| 4,226,743 A | 10/1980 | Seese et al. |
| 4,400,562 A | 8/1983 | Wagaman et al. |
| 4,499,197 A | 2/1985 | Seese et al. |
| 5,045,519 A | 9/1991 | Meyer et al. |
| 5,406,007 A | 4/1995 | Falling |
| 6,278,031 B1 | 8/2001 | Brocker et al. |
| 6,451,200 B1 | 9/2002 | Lussier et al. |
| 6,642,172 B1 | 11/2003 | Perego et al. |
| 10,196,326 B2 * | 2/2019 | Ramello ................ B01J 37/033 |
| 2005/0075239 A1 | 4/2005 | Girotti et al. |
| 2010/0330635 A1 | 12/2010 | Burgard et al. |
| 2012/0329113 A1 | 12/2012 | Burgard et al. |
| 2013/0109064 A1 | 5/2013 | Osterhout et al. |
| 2016/0184810 A1 | 6/2016 | Wright et al. |
| 2022/0161235 A1 * | 5/2022 | Nishiyama ............... B01J 21/08 |

FOREIGN PATENT DOCUMENTS

| | | |
|---|---|---|
| DE | 1150671 B | 6/1963 |
| DE | 1908620 A1 | 9/1970 |
| DE | 132126 A1 | 8/1978 |
| GB | 935631 A | 9/1963 |
| JP | S63222135 A | 9/1988 |

(Continued)

OTHER PUBLICATIONS

"D4641—17 Standard Practice for Calculation of Pore Size Distributions of Catalysts and Catalyst Carriers from Nitrogen Desorption Isotherms", ASTM International, 2017, pp. 1-7.
"The Merck Index An Encyclopedia of Chemicals and Drugs" Ninth Edition, Rahway, NJ, 1976, pp. 1-3.
C. R. Adams, "Exploratory catalytic oxidations with bismuth molybdate", Journal of Catalysis, 1968, vol. 10, pp. 355-361.
Calvin H. Bartholomew "Mechanisms of catalyst deactivation", Applied Catalysis A: General, 2001, vol. 212, pp. 17-60.
Charles R. Adams "Selectivity Effects in Some Catalytic Oxidation Processes", Industrial & Engineering Chemistry, Jun. 1969, vol. 61, No. 6, pp. 30-38.
Ekaterina V. Makshina et al. "Review of old chemistry and new catalytic advances in the on-purpose synthesis of butadiene" Royal Society of Chemistry, 2014, vol. 43, pp. 7917-7953.
Elliott P. Barrett et al. "The Determination of Pore Volume and Area Distributions in Porous Substances. I. Computations from Nitrogen Isotherms", The Volume and Area Distributions In Porous Substances, Journal of the American Chemical Society, Jan. 1951, vol. 73, No. 1, pp. 373-380.

(Continued)

*Primary Examiner* — Sharon Pregler
(74) *Attorney, Agent, or Firm* — CANTOR COLBURN LLP

(57) ABSTRACT

A process for producing a diene, preferably a conjugated diene, more preferably 1,3-butadiene, includes the steps of dehydrating at least one alkenol in the presence of at least one catalytic material having at least one acid catalyst based on silica ($SiO_2$) and alumina ($Al_2O_3$), preferably a silica-alumina ($SiO_2$—$Al_2O_3$), the catalyst having an alumina content ($Al_2O_3$) lower than or equal to 12% by weight, preferably between 0.1% by weight and 10% by weight, with respect to the catalyst total weight. The alumina content is referred to the catalyst total weight without binder, and a pore modal diameter between 9 nm and 170 nm, preferably between 10 nm and 150 nm, still more preferably between 12 nm and 120 nm.

Preferably, the alkenol is obtainable directly from biosynthetic processes, or catalytic dehydration processes of at least one diol, preferably a butanediol, more preferably 1,3-butanediol, still more preferably bio-1,3-butanediol, deriving from biosynthetic processes.

20 Claims, No Drawings

(56) References Cited

FOREIGN PATENT DOCUMENTS

| | | |
|---|---|---|
| SU | 396312 A1 | 8/1973 |
| WO | 2013130481 A1 | 9/2013 |
| WO | 2015087254 A1 | 6/2015 |
| WO | 2015173780 A1 | 11/2015 |
| WO | 2016135609 A1 | 9/2016 |
| WO | 2018073282 A1 | 4/2018 |

OTHER PUBLICATIONS

H. Gräfje et al. "Butanediols, Butenediol, and Butynediol", Ullmann's Encyclopedia of Industrial Chemistry, 2000, pp. 1-12.

International Search Report dated Mar. 5, 2021 re: Application No. PCT/IB2020/062177, pp. 1-3, citing: WO 2018/073282 A1 and WO 2016/135609 A1.

J. Haber et al. "Manual of Methods and Procedures for Catalyst Characterization", International Union of Pure and Applied Chemistry, 1995, vol. 67, Nos. 8-9, pp. 1257-1306.

J.A. Moulijn et al., "Catalyst deactivation: is it predictable? What to do?", Applied Catalysis A: General, 2001, vol. 212, pp. 3-16.

Klaus Weissermel et al. "Industrial Organic Chemistry", Third Completely Revised Edition, John Wiley & Sons, 2008, p. 117.

M. Campanati et al. "Fundamentals in the preparation of heterogeneous catalysts", Catalysis Today, 2003, vol. 77, pp. 299-314.

M. E. Winfield, "The Catalytic Dehydration of 2,3-Butanediol to Butadiene II. Adsorption Equilibria", Australian Journal of Scientific Research, 1950, vol. 3, No. 2, pp. 290-305.

Michael Bender, "An Overview of Industrial Processes for the Production of Olefins—C4 Hydrocarbons", ChemBioEng Reviews, 2014, vol. 1, No. 4, pp. 136-147, www.ChemBioEngRev.de.

Naoki Ichikawa et al. "Catalytic reaction of 1,3-butanediol over solid acids", Journal of Molecular Catalysis A: Chemical, ScienceDirect, 2006, vol. 256, pp. 106-112.

Wen Wen et al., "Effect of sol aging time on the anti-reflective properties of silica coatings 4 templated with phosphoric acid", Results in Physics, 2016, pp. 1012-1014.

Written Opinion dated Mar. 5, 2021 re: Application No. PCT/IB2020/062177, pp. 1-5, citing: WO 2018/073282 A1 and WO 2016/135609 A1.

Yoshio Uemichi et al., "Chemical recycling of poly(ethylene) by catalytic degradation into aromatic hydrocarbons using H—Ga-silicate" Chemical Communications, Department of Applied Chemistry, 1998, pp. 1975-1976.

Office Action issued by the China National IP Administration dated Oct. 7, 2023 in corresponding Chinese Application No. 202080082722.X for "Process for Producing Dienes." English translation provided. 18 pages.

* cited by examiner

PROCESS FOR PRODUCING DIENES

TECHNICAL FIELD

The present disclosure relates to a process for producing dienes.

More particularly, the present disclosure relates to a process for producing a diene, preferably a conjugated diene, more preferably 1,3-butadiene, comprising dehydrating at least one alkenol in the presence of at least one catalytic material comprising at least one acid catalyst based on silica ($SiO_2$) and alumina ($Al_2O_3$), preferably a silica-alumina ($SiO_2$—$Al_2O_3$), said catalyst having a specific alumina content ($Al_2O_3$) and specific porosity characteristics, in particular a specific pore modal diameter.

Preferably, said alkenol can be obtained directly from biosynthetic processes, or by catalytic dehydration processes of at least one diol, preferably a butanediol, more preferably 1,3-butanediol, still more preferably bio-1,3-butanediol, deriving from biosynthetic processes. Preferably, said 1,3-butadiene is bio-1,3-butadiene.

BACKGROUND

It is known that the industrial production of 1,3-butanediol, 1,3-butadiene and alkenols is currently based on classical petrochemical processes.

In fact, diols having four carbon atoms, in general, and 1,3-butanediol (generally also referred to as 1,3-BDO) in particular, are generally obtained by complex petrochemical processes as described, for example by Gräfje H. and others in "Butanediols, Butenediol, and Butynediol", "*Ulmann's Encyclopedia of Industrial Chemistry*" (2000). In particular, 1,3-butanediol is produced via acetaldehyde, hydroxy-butyraldehyde and subsequent reduction, and is generally used as a component of resins or as a solvent.

Processes for producing alkenols are also known in the art.

For example, the American patent U.S. Pat. No. 5,406,007 describes a process for preparing an allyl alcohol, a homoallyl alcohol, or a mixture thereof, comprising hydrogenating an epoxyalkene, in which the epoxy group and the ethylene unsaturation are conjugated, in the presence of a nickel catalyst modified with sulfur or sulfidate, operating under conditions of temperature and pressure that are typical for hydrogenation. Preferably, said process is useful for preparing a mixture of 2-buten-1-ol (crotyl alcohol) and 3-buten-1-ol.

The American patent U.S. Pat. No. 6,278,031 describes a process for preparing 2-buten-1-ol compounds having formula (I):

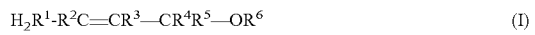

$$H_2R^1\text{-}R^2C\!=\!CR^3\!-\!CR^4R^5\!-\!OR^6 \qquad (I)$$

wherein the radicals $R^1$, $R^2$, $R^3$, $R^4$, $R^5$ and $R^6$, each independently, are hydrogen or an aliphatic radical optionally substituted with an OH, or with an OR group wherein R is an aliphatic group, a halogen or a carboxylic group, moreover $R^2$ represents a —CHO radical, or $R^2$ and $R^5$ together with the carbon atoms positioned between them form an alicyclic ring, and $R^6$ in addition represents a cycloaliphatic, araliphatic, aromatic radical or a —C(=O)—$R^7$ radical where $R^7$ is an aliphatic, cycloaliphatic, araliphatic or aromatic radical, said process comprising isomerizing 3-buten-1-ol compounds having formula (II):

$$HR^1C\!=\!CR^2\!-\!CHR^3\!-\!CR^4R^5\!-\!OR^6 \qquad (II)$$

wherein the radicals $R^1$, $R^2$, $R^3$, $R^4$, $R^5$ and $R^6$, have the same meanings described above, in the presence of hydrogen and a catalyst, wherein the process is carried out continuously on a fixed bed catalyst, wherein the catalyst comprises palladium and selenium or tellurium or a mixture of selenium and tellurium on a silicon dioxide support, and has a BET surface area of between 80 m²/g and 380 m²/g and a pore volume between 0.6 cm³/g and 0.95 cm³/g in a pore diameter between 3 nm and 300 μm, from 80% to 95% of the pore volume being in a pore diameter between 10 nm and 100 nm.

Alternatively, 2-buten-1-ol (crotyl alcohol), can be prepared by reduction of crotonaldehyde as described, for example, in "Merck Index" (1976), 9th Edition. Furthermore, 2-buten-1-ol (crotyl alcohol) can be prepared by biosynthetic processes as described, for example, in the international patent application WO 2013/130481 (as an intermediate in the synthesis of 1,3-butadiene), or in the American patent application US 2013/109064.

The American patent U.S. Pat. No. 4,400,562 describes a method for synthesizing an alkenol from 1,3-butanediol in the liquid phase comprising: mixing a sulphate of a trivalent metal selected from aluminum sulphate, chromium sulphate, iron sulphate, and mixtures thereof, as a catalyst, with 1,3-butanediol, in effective amount, obtaining a mixture of said catalyst suspended in 1,3-butanediol; heating said mixture to a temperature from about 70° C. below to about 100° C. above the boiling point of 1,3-butanediol, obtaining a partial dehydration of 1,3-butanediol into 3-buten-1-ol which evaporates from the reaction mixture; and condensing said vapour so as to isolate 3-buten-1-ol.

Alternatively, 3-buten-1-ol can be prepared from propylene and formaldehyde, with a catalyst, by operating at high temperatures, as described, for example, in the American patent application US 2013/109064.

3-Buten-2-ol (methyl vinyl carbinol) and butadiene can be obtained by dehydration of 2,3-butanediol with thorium oxide as described, for example, by Winfield M. E. in "The catalytic Dehydration of 2,3-butanediol to Butadiene. II. Adsorption Equilibria", "*Australian Journal of Scientific Research*" (1950), Vol. 3(2), pages 290-305.

Alternatively, 3-buten-2-ol (methyl vinyl carbinol), alone or in a mixture with other butenols, can be obtained, for example: by thermal decomposition of polyols or derivatives thereof (e.g., 1,3-butylene glycol diacetate) as described, for example, in the German patent DE 1,150,671; or by reduction of acetylenes or of unsaturated carbonyl compounds as described, for example, in the Russian patent SU 396312 or in the Japanese patent application JP 63/222135.

2-buten-1-ol (crotyl alcohol) can be used, for example, as a precursor of halides, crotyl esters, or crotyl ethers which, in turn, can be used, for example, as intermediates in the production of monomers, in fine chemistry (for example, for the production of sorbic acid, trimethylhydroquinone, crotonic acid, 3-methoxybutanol), in agricultural chemistry, in pharmaceutical chemistry.

3-buten-1-ol (allyl carbinol) can be used, for example, as a raw material in pharmaceutical chemistry, in agricultural chemistry, in perfumes, in resins. For example, from the coupling reaction of 3-buten-1-ol (allyl carbinol) with aryl halides, catalyzed by palladium, aryl-substituted aldehydes are obtained which can be used in pharmaceutical chemistry, for example, as antipholics.

3-buten-2-ol (methyl vinyl carbinol) can be used as a solvent, in fine chemistry, as a component in the modification of polymers such as, for example, polyolefins (as described, for example, in the German patent DE 1,908, 620).

The above alkenols can also be used for the production of 1,3-butadiene.

1,3-butadiene is a key product of petrochemicals. About ten million tons of 1,3-butadiene are produced annually and used, preferably, in the production of various products such as, for example, synthetic rubbers, resins, acrylonitrile-butadiene-styrene terpolymers (ABS), hexamethylenediamine, butanediols, in particular, 1,4-butanediol. More than 95% of 1,3-butadiene produced annually is a by-product deriving from the processes of steam cracking for the production of ethylene and other olefins and is separated by extractive distillation. Among the on purpose processes for producing 1,3-butadiene we can mention, for example, the dehydrogenation of butane and/or butenes.

The possibility of developing alternative, efficient, high-productivity processes for producing 1,3-butadiene with reduced production costs and reduced environmental impact is still of great interest. In particular, new processes able to use materials deriving from biosynthetic processes, for example bio-alkenols, in particular bio-alkenols deriving from the catalytic dehydration of bio-1,3-butanediol, to make, through a further catalytic dehydration, bio-1,3-butadiene are of great interest.

Renewable sources, biomass, syngas, or other sources of gaseous carbon can be used as carbon sources in said biosynthetic processes.

The syngas can be obtained through processes known in the art by gasification of carbon-containing materials (such as, for example, coal, biomass, waste, natural gas, and the like).

Said biosynthetic processes are generally implemented through microorganisms that are able to use carbon sources such as, for example, carbohydrates. Among the carbohydrate sources we can mention, for example, sugars (glucose, xylose, arabinose, fructose, and the like), biomasses (cellulosic, hemicellulosic ones, lignin, and the like), preferably containing carbohydrates, other renewable sources.

The production of 1,3-butadiene from diols is known in the art, but the approaches that have found industrial applications, even if in particular and/or unconventional contexts, are those based on Reppe-type technologies that use phosphate-based catalysts: in this regard, see the article by Bender M., "An Overview of Industrial Processes for the Production of Olefins—$C_4$ Hydrocarbons", "*Chem Bio Eng Reviews*" (2014), Vol. 1. No. 4, pages 136-147 (DOI: 10.1002/cben.201400016). However, said approaches are not considered industrializable today due to the low productivity, the particular reaction conditions used and the fast decay of the catalysts used, as can be seen, for example, from the documents reported below.

The American patent U.S. Pat. No. 2,310,809 describes a method for producing diolefins, in particular 1,3-butadiene, by catalytic dehydration of aliphatic glycols having at least four carbon atoms, which comprises contacting said glycols in the form of vapour, preferably with vapour or other diluting gases, with a dehydration catalyst selected from compounds containing phosphorus, capable of operating at high temperatures. The aforesaid process is said to increase the yield of diolefins, to reduce the formation of by-products and to maintain the life of the catalyst for a long time (in particular, Example 1 and Example 2, show a yield of 1,3-butadiene starting from 1,3-butanediol, equal to 85% and 90%, respectively). However, the aforesaid process is difficult to be applied industrially as very low supply speeds are used (equal to 0.060 kg×$h^{-1}$×$l^{-1}$, 60 parts of 1,3-butanediol and 40 parts of water, in the presence of n-hexane, in Example 1; and equal to 0.060 kg×$h^{-1}$×$l^{-1}$, 40 parts of 1,3-butanediol, 40 parts of water and 20 parts of 1,4-butanediol, with tetrahydrofuran, in Example 2), with consequent low productivity of the catalyst. In addition, organic, liquid substances under normal conditions, such as n-hexane are used, which are vaporized on the catalyst in order to improve the stability thereof.

The American patent U.S. Pat. No. 2,237,866 describes a process for preparing diolefins, in particular 1,3-butadiene, through the catalytic dehydration of the corresponding glycols and alcohols, in the presence of a catalyst selected from substances containing phosphorus in the vapour phase (for example, acid esters containing phosphorus, phosphorus oxychloride, phosphorus trichloride, phosphorus pentachloride).

The American patent U.S. Pat. No. 2,426,678 describes a method for regenerating dehydration catalysts based on phosphates, preferably ammonium phosphate, using volatile esters of the phosphoric acid, and ammonia ($NH_3$).

The German patent DD 132126 describes the dehydration of 1,3-butanediol into 1,3-butadiene with yields of about 90%, but with very low productivity and low supply rates (equal to 0.0375 kg×$h^{-1}$×$l^{-1}$ in Example 2).

Other approaches have not brought about better results. For example, studies on the reactivity of 2-buten-1-ol (crotyl alcohol) and on 3-buten-2-ol (methyl vinyl carbinol) to make 1,3-butadiene using bismuth molybdate type catalysts, in an oxidizing environment, are reported by Adams C. R., in "Exploratory catalytic oxidations with bismuth molybdate", "*Journal of catalysis*" (1968), Vol. 10, pages 355-361). However, bismuth molybdate is reported to be a poorly selective catalyst for the dehydration of 1,3-butanediol into 1,3-butadiene via 2-buten-1-ol (crotyl alcohol) as reported, for example, by Adams C. R., in "Selectivity Effects in Some Catalytic Oxidation Processes", "*Industrial & Engineering Chemistry*" (1969), Vol. 61(6), pages 30-38 (DOI:10.1021/ie50714a006).

Studies concerning the reactivity of alkenols to conjugated dienes other than 1,3-butadiene are also known.

For example, the American patent application U.S. Pat. No. 3,714,285 describes a process for preparing isoprene through the catalytic dehydration of 3-methyl-3-buten-1-ol (methylbutenol) comprising contacting said 3-methyl-3-buten-1-ol (methylbutenol), at high temperatures, with an acid catalyst such as phosphoric acid supported on pumice.

However, the disadvantages related to the use of catalysts based on supported phosphoric acid which require the replacement of the phosphoric acid lost during the reaction are well known. These problems are also known in other contexts, such as for example the alkylations of aromatic compounds as described, for example, in the American patent application US 2005/075239, which emphasizes the fact that said catalysts create problems of environmental impact and safety due to corrosion and disposal of the spent catalyst.

The use of different dehydration catalysts is also known in the art. For example, Weissermel K., Arpe H. J. in "*Industrial Organic Chemistry*" (2008), $3^{rd}$ Ed., John Wiley & Sons, page 117, report the Snamprogetti process for producing isoprene from acetone-acetylene, used in Italy until the 1980s, in the presence of alumina ($Al_2O_3$).

The British patent GB 935631 describes a process for preparing isoprene through the catalytic dehydration of 3-methyl-3-buten-1-ol (methylbutenol), in the vapour phase, with a catalyst consisting essentially of alumina ($Al_2O_3$)

having a surface area greater than 200 m²/g, at a temperature between 260° C. and 270° C., for a time between 1 second and 5 seconds.

It is also known the use of silica-aluminas ($SiO_2$—$Al_2O_3$) as catalysts in the production of 1,3-butadiene from alkenols as described, for example, by Sato S. and others, in "Catalytic reaction of 1,3-butanediol over solid catalyst", "*Journal of Molecular Catalysis A: Chemical*" (2006), Vol. 256, pages 106-112. In particular, Table 5 shows the values of conversion and selectivity to 1,3-butadiene obtained for 3-buten-1-ol, 2-buten-1-ol and 3-buten-2-ol, with a silica-alumina ($SiO_2$—$Al_2O_3$) as a catalyst, operating at 250° C. The values obtained are the following:

3-buten-1-ol conversion=41.5%; selectivity to 1,3-butadiene=12.8%;

2-buten-1-ol conversion=76.7%; selectivity to 1,3-butadiene=92.8%;

3-buten-2-ol conversion=70.8%; selectivity to 1,3-butadiene=93.0%.

Silica-alumina ($SiO_2$—$Al_2O_3$) used by Sato S. and others, is the product known under the trade name N631-L by Nikki Chemical, and has a surface area equal to 420 m²/g and a Si/Al ratio equal to 5.4, corresponding to an alumina content ($Al_2O_3$) of about 13% (as reported, in Example 1 of the American patent U.S. Pat. No. 3,689,477 and by Uemichi Y. and others, in "Chemical recycling of poly(ethylene) by catalytic degradation into aromatic hydrocarbons using H—Ga-silicate", "*Chemical communications*" (1998), 1975-1976 DOI:10.1039/A804927K).

However, the above-mentioned documents do not allow us to obtain useful teachings aimed at targeting industrial applications as they merely report precise data, do not address the problem of the catalyst decay, report low conversions (lower than 80%), use ideal supplies obtained from the use of commercial and non-commercial alkenols deriving from a previous dehydration reaction (for example, from the catalytic dehydration of a diol to make alkenols).

Similar conclusions can be drawn from the consultation of recent reviews such as, for example, the one by Makshina E. V. and others, "Review of old chemistry and new catalytic advances in the on-purpose synthesis of butadiene", "*Chemical Society Review*" (2014), Vol. 43, pages 7917-7953 (DOI: 10.1039/C4CS00105B).

The International patent application WO 2013/130481 describes a process for preparing 1,3-butadiene by contacting 2-buten-1-ol (crotyl alcohol) produced by a recombinant host cell therein described, with a solid acid catalyst selected, for example, from silica-aluminas ($SiO_2$—$Al_2O_3$), under the appropriate operating conditions. However, even in this case, there are no teachings relating to specific catalysts and/or specific methods of use of said catalysts.

Furthermore, from the above, it can be deduced that there is little information on the deactivation of the acid catalysts in the dehydration of alkenols. In this regard, it should be reminded that it is known that the dehydration of alcohols can occur through an acid catalysis and the main product obtained is the olefin having a number of carbon atoms corresponding to the starting alcohol, or the ether of said alcohol but in addition to said main reactions, secondary reactions can also take place such as, for example, dehydrogenation and/or oligomerization of the olefins and/or the cracking phenomena. From these secondary reactions, by-products are obtained which lead to a deactivation of the dehydration catalyst such as, for example, reported by Bartholomew C. H., in "Mechanisms of catalyst deactivation" (2001), "*Applied Catalysis A: General*" Vol. 212, p. 17-60.

An optimization of the catalytic system and of the reaction conditions is the approach that is generally followed to limit the processes leading to the deactivation of the catalyst as described, for example by Moulijn J. A. and others, in "Catalyst deactivation: is it predictable? What to do?", "*Applied Catalysis A: General*" (2001), Vol. 212, pages 3-16.

The International patent application WO 2016/135609 in the name of the Applicant describes a process for producing a diene, preferably a conjugated diene, more preferably 1,3-butadiene, comprising dehydrating at least one alkenol in the presence of at least one catalytic material comprising at least one acid catalyst based on silica ($SiO_2$) and alumina ($Al_2O_3$), preferably a silica-alumina ($SiO_2$—$Al_2O_3$), said catalyst having an alumina content lower than or equal to 12% by weight, preferably between 0.1% by weight and 10% by weight, with respect to the catalyst total weight. The use of the aforesaid catalytic material is said to allow obtaining numerous advantages. For example, said catalytic material is said to allow obtaining high conversion and selectivity values. Furthermore, said catalytic material is said to have high lifetimes, also operating at alkenols:diluent ratios included in a wide range. Furthermore, said advantages are said to remain operating in a wide range of operating conditions, i.e. at different temperatures, at different contact times ($\tau$), and allow the use of different mixtures of alkenols, i.e. both mixtures of commercial alkenols and mixtures of alkenols deriving from previous dehydration processes or directly from biosynthetic processes. Moreover, said catalytic material, when subjected to regeneration, is said to be able to be used again in the aforesaid process for producing dienes with excellent results.

Finding new processes in which an alkenol, more preferably a butenol, still more preferably bio-butenol deriving from biosynthetic processes or from precursors obtained by biosynthetic processes, is subjected to dehydration obtaining 1,3-butadiene, in particular bio-1,3- butadiene, capable of improving the aforesaid advantages, is still of great interest.

The Applicant therefore posed the problem of finding a process for producing dienes, in particular conjugated dienes, more in particular 1,3-butadiene, still more particularly bio-1,3-butadiene, by dehydration of at least one alkenol, in particular of at least one alkenol deriving from biosynthetic processes, capable of further improving the aforesaid advantages, in particular in terms of productivity of dienes, in particular of conjugated dienes, more particularly of 1,3-butadiene, still more particularly of bio-1,3-butadiene.

The Applicant has now found that some of the catalytic materials described in the aforesaid international patent application WO 2016/135609, in particular the catalytic materials comprising at least one acid catalyst based on silica ($SiO_2$) and alumina ($Al_2O_3$), in particular a silica-alumina ($SiO_2$—$Al_2O_3$), said catalyst having, in addition to the specific alumina content reported therein, specific porosity characteristics, in particular a specific pore modal diameter, can be advantageously used in the aforesaid process for producing dienes, in particular conjugated dienes, more specifically particular 1,3-butadiene, still more particularly bio-1,3-butadiene, and are able to further improve the aforesaid advantages.

SUMMARY

In particular, the Applicant has found that the use of said catalytic material allows obtaining high performances in terms of duration and consequent productivity for each reaction cycle, reducing the need for regenerations, which involve high costs and loss of production, between one cycle and another. More particularly, the use of said catalytic material is able to improve the diene productivity defined as the amount of produced diene expressed in grams, with respect to the amount of catalytic material used expressed in grams, i.e. ($g_{DIENE}/g_{CAT}$), on a single cycle, reached before the conversion drops below 80%. Still more particularly, as reported in the following examples, the use of said catalytic material is able to improve the 1,3-butadiene productivity defined as the amount of 1,3-butadiene produced expressed in grams, with respect to the amount of catalytic material used expressed in grams, i.e. ($g_{1,3-BDE}/g_{CAT}$), on a single cycle, reached before the conversion drops below 80%. Productivity on a single cycle is important as it allows to minimize catalyst regenerations, which are costly both in terms of time and in terms of lost production. Moreover, said catalytic material, when subjected to regeneration, can be used again in the aforesaid process for producing dienes with excellent results.

Therefore, the present disclosure provides a process for producing a diene, preferably a conjugated diene, more preferably 1,3-butadiene, comprising dehydrating at least one alkenol in the presence of at least one catalytic material comprising at least one acid catalyst based on silica ($SiO_2$) and alumina ($Al_2O_3$), preferably a silica-alumina ($SiO_2$—$Al_2O_3$), said catalyst having an alumina content ($Al_2O_3$) lower than or equal to 12% by weight, preferably between 0.1% by weight and 10% by weight, with respect to the catalyst total weight, said alumina content being referred to the catalyst total weight without binder, and a pore modal diameter between 9 nm and 170 nm, preferably between 10 nm and 150 nm, still more preferably between 12 nm and 120 nm.

For the purpose of the present description and the following claims, the definitions of the numerical intervals always comprise the extreme values unless otherwise specified.

For the purpose of the present description and the following claims, the term "comprising" also includes the terms "which essentially consists of" or "which consists of".

Said pore modal diameter was determined in accordance with the method BJH described by Barrett E. P., Joyner L. G. and Haklenda P. P. in "*Journal of the American Chemical Society*" (1951), Vol. 73(1), pages 373-380 (1951) and with the ASTM D4641-47 standard. In particular, said pore modal diameter was obtained from the desorption isotherm measured by the absorption and desorption of nitrogen (BET method), at the temperature of liquid nitrogen equal to −196.15° C. (77 K), plotting the pore diameter distribution curve calculated in accordance with the above BJH method. The experimental data obtained were recorded using the ASAP 2010 instrument from Micrometrics and the calculations described in the aforesaid ASTM 1.4641-17 standard were automatically carried out by the DataMaster Software™ (V4.3 Mar. 2008) supplied with said instrument assuming the predefined parameters described in the attached manual (page D-15).

DETAILED DESCRIPTION OF THE DISCLOSURE

In accordance with a preferred embodiment of the present disclosure, said alkenol can be selected, for example from: 3-buten-2-ol (methyl vinyl carbinol—CAS Number 598-32-3), 3-buten-1-ol carbinol—CAS Number 627-27-0), 2-buten-1-ol (crotyl alcohol), or mixtures thereof, preferably between 2-buten-1-ol (crotyl alcohol), 3-buten-2-ol (methyl vinyl carbinol—CAS Number 598-32-3), or mixtures thereof.

For the purpose of the present description and of the following claims, the term 2-buten-1-ol (crotyl alcohol) means: both the mixture of the cis and trans isomers, and the cis isomer as such (CAS Number 4088-60-2), as well as the trans isomer as such (CAS Number 504-61-0).

In accordance with a preferred embodiment of the present disclosure, said alkenol can be obtained directly from biosynthetic processes, or by catalytic dehydration processes of at least one diol, preferably a butanediol, more preferably 1,3-butanediol, still more preferably bio-1,3-butanediol, deriving from biosynthetic processes.

Biosynthetic processes capable of directly making alkenols are described, for example, in the International patent application WO 2013/130481, or in the American patent application US 2013/109064, reported above.

For the purpose of the present disclosure, said alkenol can be obtained by catalytic dehydration of at least one diol, preferably of at least one butanediol, more preferably 1,3-butanediol, still more preferably bio-1,3-butanediol deriving from biosynthetic processes, in the presence of at least one catalyst based on cerium oxide, in which said catalyst based on cerium oxide is obtained by precipitation, in the presence of at least one base, of at least one compound containing cerium. Further details relating to said process can be found in the International patent application WO 2015/173780 in the name of the Applicant and incorporated herein by reference.

In accordance with a particularly preferred embodiment of the present disclosure, said alkenol derives from the catalytic dehydration of at least one diol, preferably a butanediol, more preferably 1,3-butanediol, still more preferably bio-1,3-butanediol, deriving from sugar fermentation, preferably from the fermentation of sugars deriving from biomass.

For the purpose of the present description and of the following claims, the term "biomass" indicates any organic material of vegetable origin including: products deriving from agriculture such as, for example, guayule, thistle, corn, soy, cotton, flax, rapeseed, sugar cane, palm, including scraps, residues and waste deriving from said products or from the processing thereof; products deriving from crops specifically cultivated for energy use such as, for example, miscanthus, panic, common reed, including scraps, residues and waste deriving from said products or from the processing thereof; products deriving from afforestation or forestry including scraps, residues and waste deriving from said products or from the processing thereof; scraps from agrofood products intended for human consumption or zootechnics; residues from the paper industry; waste coming from the separate collection of municipal solid waste such as, for example, urban waste of vegetable origin, paper.

Preferably, said diol is bio-1,3-butanediol deriving from the fermentation of sugars deriving from biomass, including scraps, residues, waste deriving from said biomass or from the processing thereof.

Still more preferably, said diol is bio-1,3-butanediol deriving from the fermentation of sugars deriving from guayule, including scraps, residues, waste deriving from said guayule or from the processing thereof.

In the case of use of a ligninocellulosic biomass of vegetable origin, in order to produce sugars, said biomass is subjected to physical treatments (such as, extrusion, "steam explosion", and the like), and/or to chemical hydrolysis and/or to enzymatic hydrolysis, obtaining mixtures of carbohydrates, aromatic compounds and of other products deriving from the cellulose, hemicellulose and lignin present in the biomass. In particular, the obtained carbohydrates are mixtures of sugars with 5 and 6 carbon atoms which include, for example, sucrose, glucose, xylose, arabinose, galactose, mannose and fructose, which will be used in the fermentation. Processes relating to the production of sugars from biomass are described in the art such as for example, in the International patent application WO 2015/087254, in the name of the Applicant. Said fermentation is generally implemented by microorganisms, in particular by genetically modified microorganisms, capable of producing the alcohols of interest. More details relating to processes for the synthesis of 1,3-butanediol, in particular bio-1,3-butanediol, starting from renewable sources can be found, for example, in the American patent applications US 2010/330635, US 2012/0329113 and US 2013/0109064.

If the diol derives from biosynthetic processes, for example, from the fermentation of sugars, the aqueous mixture of alkenols obtained can be subjected to separation processes known in the art such as, for example, total or partial distillation. Alternatively, said aqueous mixture of alkenols can be used as such, effectively using water as a diluent, with no need to subject said aqueous mixture to expensive water elimination processes or, in any case, limiting said elimination.

It should be noted that, in the case in which said alkenol derives from the catalytic dehydration of at least one diol, the dehydration of said at least one diol to give at least one alkenol and the subsequent dehydration of said at least one alkenol to give a diene, can be implemented:
  in the same reactor or in different reactors, preferably in different reactors;
  continuously or discontinuously, preferably discontinuously.

For the purpose of the present disclosure, said acid catalyst based on silica ($SiO_2$) and alumina ($Al_2O_3$), can be obtained by processes known in the art and can be used in various forms as described, for example, in the International patent application WO 2016/135069 reported above in the name of the Applicant and incorporated therein by reference. Further details relating to the processes for preparing said catalyst can also be found in the following examples.

For the purpose of the present disclosure, said acid catalyst based on silica ($SiO_2$) and alumina ($Al_2O_3$), can be used as such, or it can be bound and/or formed by operating according to any process known in the art. Further details relating to said processes can be found, for example, in the American patents U.S. Pat. Nos. 3,974,099, 4,226,743, 6,451,200, 4,499,197, 4,175,118, 5,045,519, 6,642,172; or in: Campanati M. and others, "Fundamentals in the preparation of heterogeneous catalysts", "*Catalysis Today*" (2003), Vol. 77, pages 299-314; Haber J. and others, "Manual of methods and procedures for catalyst characterization", "*Pure & Applied Chemistry*" (1995), Vol. 67. No. 8-9, pages 1257-1306.

In accordance with a preferred embodiment of the present disclosure, said acid catalyst based on silica ($SiO_2$) and alumina ($Al_2O_3$) can be obtained by "incipient wetness impregnation" wherein the volume of a solution of at least one alumina precursor that can be selected, for example, from aluminum alkoxides (for example, tri-sec-aluminium butoxide), soluble aluminum salts (for example, aluminum sulphate), aluminates (for example, sodium aluminate), in a suitable concentration, is equal to or slightly lower than the pore volume of a solid support (for example, silica).

In accordance with a further preferred embodiment of the present disclosure, said catalytic material comprising at least one acid catalyst based on silica ($SiO_2$) and alumina ($Al_2O_3$), can be obtained by a process comprising:
  preparing an aqueous solution or an aqueous suspension of alumina ($Al_2O_3$) or of at least one precursor thereof that can be selected, for example, from aluminum alkoxides (for example, tri-sec-aluminium butoxide), soluble aluminum salts (for example, aluminum sulphate), aluminates (for example, sodium aluminate);
  adding to said aqueous solution or aqueous suspension of alumina ($Al_2O_3$) or of at least one precursor thereof, an aqueous solution or an aqueous suspension of silica ($SiO_2$) or of at least one precursor thereof that can be selected from silicic acids (for example, orthosilicic acid), alkali metal silicates (for example, sodium silicate);
  recovering the solid obtained by precipitation, or gelation, and optionally subjecting it:
    to an ion exchange step with at least one compound capable of exchanging ions with the surface of the obtained solid that can be selected, for example, from aqueous solutions of salts containing ammonium ions (for example, ammonium acetate, ammonium nitrate, ammonium sulphate); and/or
    to a binding step with at least one silica precursor ($SiO_2$) that can be selected, for example, from colloidal silicas (for example, Ludox® TMA"—Sigma-Aldrich), silica alkoxides (for example, tetraethylorthosilicate); or of at least one alumina precursor ($Al_2O_3$) that can be selected, for example, from bohemite or pseudo-bohemite (for example, Versal™ V-250—UOP); and/or
    to a forming step such as, for example, extrusion, spherulization, tableting, granulation;
  subjecting it to optional thermal treatment and/or optional calcination, said optional thermal treatment and/or optional calcination being carried out before or after one of the aforesaid steps, that is ion exchange, and/or binding, and/or forming.

It should be noted that, for the purpose of the present disclosure, said aqueous solution or aqueous suspension of alumina ($Al_2O_3$) or of at least one precursor thereof, can be added in one or more steps to said aqueous solution or aqueous suspension of silica ($SiO_2$) or of at least one of the precursors thereof.

It should be noted that, for the purpose of the present disclosure, said aqueous solution or aqueous suspension of alumina ($SiO_2$) or of at least one precursor thereof, can be added in one or more steps to said aqueous solution or aqueous suspension of silica ($Al_2O_3$) or at least one of the precursors thereof.

The additions described above can be carried out using methods known in the art, as well as referring to normal laboratory practices (by way of example, but not limiting to the scope of the present disclosure, by weighing, by volumetric dosages, etc.). The addition steps can however be greater than two without however constituting a criticality and, therefore, a limitation of the present disclosure.

For the purpose of the present disclosure, said aqueous solution or aqueous suspension of alumina ($Al_2O_3$) or of at least one precursor thereof, can comprise from 0.1% by weight to 70% by weight, preferably from 0.3% by weight to 60% by weight, still more preferably from 0.5% by weight to 50% by weight, with respect to the total weight of said aqueous solution or aqueous suspension of alumina ($Al_2O_3$) or of at least one precursor thereof.

Alternatively, instead of said aqueous solution or aqueous suspension of alumina ($Al_2O_3$) or of at least one precursor thereof, a hydroalcoholic solution comprising from 0.1% by weight to 95% by weight, preferably from 0.3% by weight to 60% by weight, still more preferably from 0.5%, by weight to 30% by weight, with respect to the total weight of said hydroalcoholic solution, of at least one alcohol selected, for example, from ethanol, 2-methoxyethanol, n-propanol, iso-propanol, n-butanol, iso-butanol, tert-butanol, or mixtures thereof can be used.

For the purpose of the present disclosure, said aqueous solution or aqueous suspension of silica ($SiO_2$) or of at least one precursor thereof, can comprise from 5% by weight to 70% by weight, preferably from 10% by weight to 60% by weight, still more preferably from 15% by weight to 50% by weight, with respect to total weight of said aqueous solution or aqueous suspension, of silica ($SiO_2$) or at least one precursors thereof.

Alternatively, instead of said aqueous solution or aqueous suspension of silica ($SiO_2$) or of at least one precursor thereof, a hydroalcoholic solution comprising from 5% by weight to 95% by weight, preferably from 15% by weight to 60% by weight, still more preferably from 20% by weight to 30% by weight, with respect to the total weight of said hydroalcoholic solution, of at least one alcohol selected, for example, from ethanol, 2-methoxyethanol, n-propanol, iso-propanol, n-butanol, iso-butanol, tert-butanol, or mixtures thereof can be used.

The solid obtained by the aforesaid process can be recovered through processes known in the art such as, for example, filtration, decantation, and the like.

The aforesaid possible heat treatment can be carried out at a temperature between 100° C. and 200° C., preferably between 105° C. and 150° C., for a time between 2 hours and 72 hours, preferably between 3 hours and 18 hours.

The aforesaid optional calcination can be carried out at a temperature between 150° C. and 1500° C., preferably between 200° C. and 1400° C., still more preferably between 300° C. and 1200° C., for a time between 1 hour and 24 hours, preferably between 2 hours and 10 hours, still more preferably between 4 hours and 8 hours. Generally, said calcination can be carried out in the air, or with an inert gas [such as nitrogen ($N_2$)], or in a controlled atmosphere (oxidizing or reducing), preferably in air.

As stated above, the acid catalyst based on silica ($SiO_2$) and alumina ($Al_2O_3$), when not obtained by incipient wetness impregnation, can be used in various forms. For example, said catalyst can be used as such, or it can be formed by operating according to any forming process known in the art such as, for example, extrusion, spherulation, tableting, granulation, and the like. The optional heat treatment and the optional calcination reported above can be carried out before or after one of said forming processes.

Preferably, said acid catalyst based on silica ($SiO_2$) and alumina ($Al_2O_3$), when not obtained by incipient wetness impregnation, can be used in extruded form, optionally containing traditional binders such as, for example, alumina ($Al_2O_3$), silica ($SiO_2$), zirconium oxide, titanium oxide, preferably silica ($SiO_2$) or alumina ($Al_2O_3$), still more preferably alumina ($Al_2O_3$).

If said traditional binders are present, the extrusion generally also provides for the use of a peptizing agent such as, for example, aqueous solutions of acetic acid, nitric acid, or ammonium hydroxide, which can be mixed with the catalyst and the binder before extrusion, until a homogeneous mixture is obtained. At the end of said extrusion, the pellets obtained are generally subjected to calcination by operating as described above.

The solid obtained after binding and/or forming can contain from 5% by weight to 90% by weight, preferably from 10% by weight to 75% by weight, more preferably from 20% by weight to 55% by weight, of binder, with respect to the total weight of said acid catalyst based on silica ($SiO_2$) and alumina ($Al_2O_3$).

It should be noted that after binding and/or forming said catalytic material comprising at least one acid catalyst based on silica ($SiO_2$) and alumina ($Al_2O_3$) has a pore modal diameter in the range reported above, i.e. a pore modal diameter between 9 nm and 170 nm, preferably between 10 nm and 150 nm, still more preferably between 12 nm and 120 nm.

In accordance with a preferred embodiment of the present disclosure, said catalytic material comprising at least one acid catalyst based on silica ($SiO_2$) and alumina ($Al_2O_3$), obtained after binding and/or forming, has a pore modal diameter between 9 nm and 170 nm, preferably between 10 nm and 150 nm, still more preferably between 12 nm and 120 nm.

In accordance with a preferred embodiment of the present disclosure, said acid catalyst based on silica ($SiO_2$) and alumina ($Al_2O_3$) can have a specific surface area between 40 $m^2/g$ and 800 $m^2/g$, preferably between 45 $m^2/g$ and 700 $m^2/g$, still more preferably between 50 $m^2/g$ and 600 $m^2/g$.

In accordance with a preferred embodiment of the present disclosure, said catalytic material comprises at least one acid catalyst based on silica ($SiO_2$) and alumina ($Al_2O_3$) and at least one binder that can be selected, for example, from alumina ($Al_2O_3$), silica ($SiO_2$), zirconium oxide, titanium oxide, preferably silica ($SiO_2$) or alumina ($Al_2O_3$), still more preferably alumina ($Al_2O_3$).

In accordance with a further preferred embodiment of the present disclosure, said catalytic material comprising at least one acid catalyst based on silica ($SiO_2$) and alumina ($Al_2O_3$), and at least one binder selected from alumina ($Al_2O_3$) or silica ($SiO_2$), and/or subjected to forming, can have a specific surface area between 25 $m^2/g$ and 700 $m^2/g$, preferably between 100 $m^2/g$ and 600 $m^2/g$, still more preferably between 110 $m^2/g$ and 500 $m^2/g$.

For the purpose of the present description and of the following claims, the term "specific surface area" indicates the BET specific surface area determined by static absorption of nitrogen ($N_2$), at the temperature of the liquid nitrogen equal to −196.15° C. (77 K), with ASAP 2010 instrument from Micromeritics, in accordance with the ASTM D3663-03 (2008) standard.

The elementary analysis of said acid catalyst based on silica ($SiO_2$) and alumina ($Al_2O_3$), was carried out via WD-XRF ("Wavelength dispersion X Ray fluorescence"), with a PANalytical Axios Advanced spectrometer equipped with a 4 KW X-ray tube with rhodium (Rh) anode.

In accordance with a preferred embodiment of the present disclosure, said process for producing a diene can be carried out with at least one diluent that can be selected, for example, from: inert gases such as, for example, nitrogen ($N_2$), argon (Ar), preferably nitrogen ($N_2$); or from compounds having a boiling temperature higher than or equal to 50° C. and a melting temperature lower than or equal to 40° C., that are, preferably, in the liquid state at ambient temperature (25° C.) and at ambient pressure (1 atm), such as, for example, water, tetrahydrofuran, cyclohexane, benzene. Nitrogen ($N_2$), water, are preferred, water is particularly preferred.

In accordance with a preferred embodiment of the present disclosure, said process for producing a diene can be carried out, in case the diluent is selected from inert gases, at a molar ratio of diluent to alkenol/s greater than 0.3, preferably between 0.5 and 2.

In accordance with a preferred embodiment of the present disclosure, said process for producing a diene can be carried out, in case the diluent is selected from compounds having a boiling temperature higher than or equal to 50° C. and a melting temperature lower than or equal to 40° C., that are preferably, in the liquid state at ambient temperature (25° C.) and at ambient pressure (1 atm), at a molar ratio of diluent to alkenol/s between 0.01 and 100, preferably between 0.1 and 50, more preferably between 1 and 10.

In accordance with a preferred embodiment of the present disclosure, said process for producing a diene can be carried out at a temperature between 150° C. and 500° C., preferably between 200° C. and 450° C., more preferably between 250° C. and 400° C.

In accordance with a preferred embodiment of the present disclosure, said process for producing a diene can be carried out at a pressure between 0.05 bara and 50 bara, preferably between 0.3 bara and 3,5 bara, more preferably between 0.8 bara and 2.5 bara (bara=absolute bars).

In accordance with a preferred embodiment of the present disclosure, said process for producing a diene can be carried out by operating at a contact time ($\tau$), calculated as the ratio of the catalytic material loaded to feeding volumetric rate, between 0.01 seconds and 10 seconds, preferably between 0.05 seconds and 8 seconds, more preferably between 0.1 seconds and 4 seconds.

In accordance with a preferred embodiment of the present disclosure, said catalytic material comprising at least one acid catalyst based on silica ($SiO_2$) and alumina ($Al_2O_3$), preferably a silica-alumina ($SiO_2$—$Al_2O_3$), can be pre-treated at the temperature to which said process for producing a diene is carried out, that is at a temperature between 150° C. and 500° C., preferably between 200° C. and 450° C., more preferably between 250° C. and 400° C., preferably in the presence of at least one diluent selected from those reported above, more preferably in the presence of water.

For the purpose of the present disclosure, said process for producing a diene can be carried out in the gas phase or in the mixed liquid/gas phase, preferably in the gas phase, discontinuously (for example, in a stirred and heated autoclave), or continuously (for example, in one or more catalytic reactors in series), preferably continuously. Said reactors can be with fixed bed, or with fluidized bed, preferably with fixed bed. If they are with fixed bed, the catalytic material can be divided into several beds. Said reactors can contemplate a recycling of part of the reaction effluents or of the catalytic material by configuring a recirculated reactor. If a liquid phase is present, the process for producing dienes can be carried out in continuous stirring reactors, containing the dispersed catalytic material.

In order to better understand the present disclosure and to put it into practice, some illustrative and non-limiting examples thereof are reported below.

Example 1 (Comparative)

Preparation of a Silica-Alumina ($SiO_2$—$Al_2O_3$) Having an Alumina Content ($Al_2O_3$) Equal to 1.8% and Pore Modal Diameter Equal to 7 nm 3360.3 g of an aqueous solution of sodium silicate having a silica content ($SiO_2$) equal to 26.5% (Aldrich), as a silica precursor ($SiO_2$) were introduced into a first 5 l flask. In a second 2 l flask, 26.6 g of sodium aluminate (Aldrich), as an alumina precursor ($Al_2O_3$), and 650.9 g of demineralized water, were introduced obtaining a second aqueous solution. Said second aqueous solution was poured into the 5 l flask and the resulting solution was kept under vigorous stirring (500 rpm), at ambient temperature (25° C.), for 1 hour, obtaining a suspension which was subsequently heated to 80° C., and kept under vigorous stirring (500 rpm), at said temperature, for 1 hour. After cooling to ambient temperature (25° C.), the pH of the suspension obtained was brought from pH 13 to pH 12 by adding a 96% sulfuric acid solution (Aldrich), obtaining a colourless gel. The gel obtained was granulated, transferred to a 12 l plastic container and treated 4 times with 500 ml of an aqueous solution of 10% ammonium sulphate (Aldrich). The material was filtered, washed with 10 l of demineralized water, dried at 120° C. for one night, and subsequently calcined at 500° C., for 5 hours, obtaining a silica-alumina ($SiO_2$—$Al_2O_3$) in the form of colourless powder (936 g), the elemental analysis of which, carried out as described above, showed an alumina content ($Al_2O_3$) equal to 1.8%. Said silica-alumina ($SiO_2$—$Al_2O_3$) had a specific BET surface area, determined as reported above, equal to 259 m$^2$/g, and pore modal diameter, determined as reported above, equal to 7 nm.

Example 2 (Comparative)

Preparation of a Catalyst Based on Silica-Alumina ($SiO_2$—$Al_2O_3$) Having an Alumina Content ($Al_2O_3$) Equal to 1.8%, with Alumina Binder ($Al_2O_3$) and Pore Modal Diameter Equal to 3 nm A part of the silica-alumina ($SiO_2$—$Al_2O_3$) obtained in Example 1, 63.8 g, was mixed with 30.8 g of pseudoboemite Versal™ V-250 (UOP), as an alumina precursor ($Al_2O_3$) of the binder, and 300 ml of a 4% solution of acetic acid (Aldrich) in a 500 ml beaker. The obtained mixture was kept, under vigorous stirring (500 rpm), at 60° C., for about 2 hours. Subsequently, the beaker was transferred onto a heating plate and the mixture was kept, under vigorous stirring (500 rpm), at 150° C., for one night, until dry. The solid obtained was calcined at 550° C. for 5 hours, obtaining a silica-alumina ($SiO_2$—$Al_2O_3$) with alumina binder ($Al_2O_3$) in the form of a colourless solid (84 g) which was subsequently mechanically granulated and the fraction of granules having dimensions from 0.5 mm to 1.0 mm was used as the catalytic material. Said silica-alumina ($SiO_2$—$Al_2O_3$) with alumina binder ($Al_2O_3$) had a specific BET surface area, determined as reported above, equal to 254 m$^2$/g and pore modal diameter, determined as reported above, equal to 3 nm.

Example 3 (Disclosure)

Preparation of a Silica-Alumina ($SiO_2$—$Al_2O_3$) Having an Alumina Content ($Al_2O_3$) Equal to 1.8% and Pore Modal Diameter Equal to 14 nm 1056.8 g of an aqueous solution of sodium silicate having a silica content ($SiO_2$) equal to 26.5% (Aldrich), as a silica precursor ($SiO_2$) and 786.6 g of demineralized water were introduced into a first 5 l flask. In a second 2 l flask, 8.5 g of sodium aluminate (Aldrich), as an alumina precursor ($Al_2O_3$), and 1199.1 g of demineralized water, were introduced obtaining a second aqueous solution. Said second aqueous solution was poured into the 5 l flask and the resulting solution was kept under vigorous stirring (500 rpm), at ambient temperature (25° C.), for 1 hour, obtaining a suspension which was subsequently heated to 80° C., and kept under vigorous stirring (500 rpm), at said temperature, for 1 hour. After cooling to ambient temperature (25° C.), the pH of the suspension obtained was brought from pH 13 to pH 8.5 by adding a 96% sulfuric acid solution (Aldrich), obtaining a colourless gel. The gel obtained was transferred to a 12 l plastic container and treated 4 times with 5 kg of an aqueous solution of 10% ammonium sulphate (Aldrich), obtaining a solid. Said solid was filtered, washed with 10 kg of demineralized water, dried at 120° C. for one night, and subsequently calcined at 500° C., for 5 hours, obtaining a silica-alumina ($SiO_2$—$Al_2O_3$) in the form of colourless powder (236 g), the elemental analysis of which, carried out as described above, showed an alumina content ($Al_2O_3$) equal to 1.8%. Said silica-alumina ($SiO_2$—$Al_2O_3$) had a specific BET surface area, determined as reported above, equal to 262 m$^2$/g, and pore modal diameter, determined as reported above, equal to 14 nm.

Example 4 (Disclosure)

Preparation of a Catalyst Based on Silica-Alumina ($SiO_2$—$Al_2O_3$) Having an Alumina Content ($Al_2O_3$) Equal to 1.8%, with Alumina Binder ($Al_2O_3$) and Pore Modal Diameter Equal to 14 nm A part of the silica-alumina ($SiO_2$—$Al_2O_3$) obtained in Example 3, 26.6 g, was mixed with 14.7 g of pseudoboemite Versal™ V-250 (UOP), as an alumina precursor ($Al_2O_3$) of the binder, and 300 ml of a 4% solution of acetic acid (Aldrich) in a 500 ml beaker. The obtained mixture was kept, under vigorous stirring (500 rpm), at 60° C., for about 2 hours. Subsequently, the beaker was transferred onto a heating plate and the mixture was kept, under vigorous stirring (500 rpm), at 150° C., for one night, until dry. The solid obtained was calcined at 550° C. for 5 hours, obtaining a silica-alumina ($SiO_2$—$Al_2O_3$) with alumina binder ($Al_2O_3$) in the form of a colourless solid (34 g) which was subsequently mechanically granulated and the fraction of granules having dimensions from 0.5 mm to 1.0 mm was used as the catalytic material. Said silica-alumina ($SiO_2$—$Al_2O_3$) with alumina binder ($Al_2O_3$) had a specific BET surface area, determined as reported above, equal to 255 m$^2$/g and pore modal diameter, determined as reported above, equal to 14 nm.

Example 5 (Disclosure)

Preparation of a Silica-Alumina ($SiO_2$—$Al_2O_3$) Having an Alumina Content ($Al_2O_3$) Equal to 1.8% and Pore Modal Diameter Equal to 40 nm 1057.3 g of an aqueous solution of sodium silicate having a silica content ($SiO_2$) equal to 26.5% (Aldrich), as a silica precursor ($SiO_2$) and 787.0 g of demineralized water were introduced into a first 5 l flask. In a second 2 l flask, 9.0 g of sodium aluminate (Aldrich), as an alumina precursor ($Al_2O_3$), and 1219.8 g of demineralized water, were introduced obtaining a second aqueous solution. Said second aqueous solution was poured into the 5 l flask and the resulting solution was kept under vigorous stirring (500 rpm), at ambient temperature (25° C.), for 1 hour, obtaining a suspension which was subsequently heated to 80° C., and kept under vigorous stirring (500 rpm), at said temperature, for 1 hour. After cooling to ambient temperature (25° C.), the pH of the suspension obtained was brought from pH 13 to pH 8.5 by adding a 96% sulfuric acid solution (Aldrich), and the whole was kept under stirring, at ambient temperature (25° C.), for 72 hours, obtaining a colourless gel. The colourless gel obtained was transferred to a 12 l plastic container and treated 4 times with 5 kg of an aqueous solution of 10% ammonium sulphate (Aldrich), obtaining a solid. Said solid was filtered, washed with 10 kg of demineralized water, dried at 120° C. for one night, and subsequently calcined at 500° C., for 5 hours, obtaining a silica-alumina ($SiO_2$—$Al_2O_3$) in the form of colourless powder (252.8 g), the elemental analysis of which, carried out as described above, showed an alumina content ($Al_2O_3$) equal to 1.8%. Said silica-alumina ($SiO_2$—$Al_2O_3$) had a specific BET surface area, determined as reported above, equal to 221 m$^2$/g, and pore modal diameter, determined as reported above, equal to 40 nm.

Example 6 (Disclosure)

Preparation of a Catalyst Based on Silica-Alumina ($SiO_2$—$Al_2O_3$) Having an Alumina Content ($Al_2O_3$) Equal to 1.8% and Pore Modal Diameter Equal to 37 nm, with Alumina Binder ($Al_2O_3$)

A part of the silica-alumina ($SiO_2$—$Al_2O_3$) obtained in Example 5, 100.1 g, was mixed with 55.2 g of pseudoboemite Versal™ V-250 (UOP), as an alumina precursor ($Al_2O_3$) of the binder, and 300 ml of a 4% solution of acetic acid (Aldrich) in a 500 ml beaker. The obtained mixture was kept, under vigorous stirring (500 rpm), at 60° C., for about 2 hours. Subsequently, the beaker was transferred onto a heating plate and the mixture was kept, under vigorous stirring (500 rpm), at 150° C., for one night, until dry. The solid obtained was calcined at 550° C. for 5 hours, obtaining a silica-alumina ($SiO_2$—$Al_2O_3$) with alumina binder ($Al_2O_3$) in the form of a colourless solid (138 g) which was subsequently mechanically granulated and the fraction of granules having dimensions from 0.5 mm to 1.0 mm was used as the catalytic material. Said silica-alumina ($SiO_2$—$Al_2O_3$) with alumina binder ($Al_2O_3$) had a specific BET surface area, determined as reported above, equal to 212 m$^2$/g and pore modal diameter, determined as reported above, equal to 37 nm.

Example 7 (Disclosure)

Preparation of a Silica-Alumina ($SiO_2$—$Al_2O_3$) Having an Alumina Content ($Al_2O_3$) Equal to 1.8% and Pore Modal Diameter Equal to 37 nm 1056.9 g of an aqueous solution of sodium silicate having a silica content ($SiO_2$) equal to 26.5% (Aldrich), as a silica precursor ($SiO_2$) and 787.9 g of demineralized water were introduced into a first 5 l flask. In a second 2 l flask, 9.0 g of sodium aluminate (Aldrich), as an alumina precursor ($Al_2O_3$), and 1219.2 g of demineralized water, were introduced obtaining a second aqueous solution. Said second aqueous solution was poured into the 5 l flask and the resulting solution was kept under vigorous stirring (500 rpm), at ambient temperature (25° C.), for 1 hour, obtaining a suspension which was subsequently heated to 80° C., and kept under vigorous stirring (500 rpm), at said temperature, for 1 hour. After cooling to ambient temperature (25° C.), the pH of the suspension obtained was brought from pH 13 to pH 8.5 by adding a 70% nitric acid solution (Aldrich), and the whole was kept under stirring, at ambient temperature (25° C.), for 72 hours, obtaining a colourless gel. The colourless gel obtained was transferred to a 12 l plastic container and treated 4 times with 5 kg of an aqueous solution of 10% ammonium sulphate (Aldrich), obtaining a solid. Said solid was filtered, washed with 10 kg of demineralized water, dried at 120° C. for one night, and subsequently calcined at 500° C., for 5 hours, obtaining a silica-alumina ($SiO_2$—$Al_2O_3$) in the form of colourless powder (254.5 g), the elemental analysis of which, carried out as described above, showed an alumina content ($Al_2O_3$) equal to 1.8%. Said silica-alumina ($SiO_2$—$Al_2O_3$) had a specific BET surface area, determined as reported above, equal to 252 $m^2/g$, and pore modal diameter, determined as reported above, equal to 37 nm.

Example 8 (Disclosure)

Preparation of a Catalyst Based on Silica-Alumina ($SiO_2$—$Al_2O_3$) Having an Alumina Content ($Al_2O_3$) Equal to 1.8% and Pore Modal Diameter Equal to 36 nm, with Alumina Binder ($Al_2O_3$) (Extruded)

A part of the silica-alumina ($SiO_2$—$Al_2O_3$), obtained in Example 7, was subjected to an extrusion process. For this purpose, 100.1 g of said silica-alumina ($SiO_2$—$Al_2O_3$) and 86.6 g of pseudoboemite Versal™ V-250 (UOP), as an alumina precursor ($Al_2O_3$), of the binder were introduced into an Erweka AR 402 mixer: the powders were mixed at a rotation speed of 80 rpm, for 2 hours. Subsequently, 253.0 g of a 5% solution of acetic acid were supplied: the mixture obtained was kept at a rotation speed of 80 rpm, for a further 2 hours. Subsequently, the mixture was transferred to a Hosokawa-Bepex Pharmapaktor L 200/50 G laboratory extruder, operating under the following conditions:
 temperature: 25° C.;
 rotation speed of the screws:15 rpm;
 applied force:150 kN.

Pellets were obtained at the exit from the extruder which were dried in the air, then calcined at 550° C. for 5 hours. 133.7 silica-alumina ($SiO_2$—$Al_2O_3$) with alumina binder ($Al_2O_3$) in the form of a colourless solid was obtained which was subsequently mechanically granulated and the fraction of granules having dimensions from 0.5 mm to 1.0 mm was used as the catalytic material. Said silica-alumina ($SiO_2$—$Al_2O_3$) with alumina binder ($Al_2O_3$) had a specific BET surface area, determined as reported above, equal to 260 $m^2/g$ and pore modal diameter, determined as reported above, equal to 36 nm.

Example 9 (Disclosure)

Preparation of a Silica-Alumina ($SiO_2$—$Al_2O_3$) Having an Alumina Content ($Al_2O_3$) Equal to 1.8% and Pore Modal Diameter Equal to 100 nm 251.4 g of an aqueous solution of sodium silicate having a silica content ($SiO_2$) equal to 26.5% (Aldrich), as a silica precursor ($SiO_2$) and 105.0 g of demineralized water are introduced into a first 1 l flask. In a second 1 l flask, 1.8 g of sodium aluminate (Aldrich), as an alumina precursor ($Al_2O_3$), 11.1 g of sodium dihydrogen phosphate ($NaH_2PO_4.H_2O$) (Aldrich) and 255.0 g of demineralized water were introduced obtaining a second aqueous solution. Said second aqueous solution was poured into the 1 l flask and the resulting solution was kept under vigorous stirring (500 rpm), at ambient temperature (25° C.), for 1 hour, obtaining a suspension which was subsequently heated to 80° C., and kept under vigorous stirring (500 rpm), at said temperature, for 1 hour. After cooling to ambient temperature (25° C.), the pH of the suspension obtained was brought from pH 13 to pH 8.5 by adding a 96% sulfuric acid solution (Aldrich), obtaining a colourless gel. The gel obtained was transferred to a 5 l plastic container and treated 4 times with 2 kg of an aqueous solution of 10% ammonium acetate (Aldrich), obtaining a solid. Said solid was filtered, washed with 500 g of demineralized water, dried at 120° C. for one night, and subsequently calcined at 500° C., for 5 hours, obtaining a silica-alumina ($SiO_2$—$Al_2O_3$) in the form of colourless powder (54 g), the elemental analysis of which, carried out as described above, showed an alumina content ($Al_2O_3$) equal to 1.8%. Said silica-alumina ($SiO_2$—$Al_2O_3$) had a specific BET surface area, determined as reported above, equal to 57 $m^2/g$, and pore modal diameter, determined as reported above, equal to 100 nm.

Example 10 (Disclosure)

Preparation of a Catalyst Based on Silica-Alumina ($SiO_2$—$Al_2O_3$) Having an Alumina Content ($Al_2O_3$) Equal to 1.8% and Pore Modal Diameter Equal to 100 nm, with Alumina Binder ($Al_2O_3$)

A part of the silica-alumina ($SiO_2$—$Al_2O_3$) obtained in Example 9, 20.0 g, was mixed with 12.0 g of pseudoboemite Versal™ V-250 (UOP), as an alumina precursor ($Al_2O_3$) of the binder, and 300 ml of a 4% solution of acetic acid (Aldrich) in a 500 ml beaker. The obtained mixture was kept, under vigorous stirring (500 rpm), at 60° C., for about 2 hours. Subsequently, the beaker was transferred onto a heating plate and the mixture was kept, under vigorous stirring (500 rpm), at 150° C., for one night, until dry. The solid obtained was calcined at 550° C. for 5 hours, obtaining a silica-alumina ($SiO_2$—$Al_2O_3$) with alumina binder ($Al_2O_3$) in the form of a colourless solid (28 g) which was subsequently mechanically granulated and the fraction of granules having dimensions from 0.5 mm to 1.0 mm was used as the catalytic material. Said silica-alumina ($SiO_2$—$Al_2O_3$) with alumina binder ($Al_2O_3$) had a specific BET surface area, determined as reported above, equal to 118 $m^2/g$ and pore modal diameter, determined as reported above, equal to 100 nm.

Example 11 (Comparative)

Preparation of a Catalyst Based on Silica-Alumina ($SiO_2$—$Al_2O_3$) Having an Alumina Content ($Al_2O_3$) Equal to 1.8% and Pore Modal Diameter Equal to 3 nm (Extruded)

A part of the silica-alumina ($SiO_2$—$Al_2O_3$), prepared in Example 1, was subjected to an extrusion process.

For this purpose, 450.1 g of said silica-alumina ($SiO_2$—$Al_2O_3$) and 217.0 g of pseudoboemite Versal™ V-250 (UOP), as an alumina precursor ($Al_2O_3$), of the binder were introduced into an Erweka AR 402 planetary mixer. The powders were mixed at a rotation speed equal to 80 rpm, for 2 hours. Subsequently, keeping the rotation speed equal to 80 rpm in the mixer, 766.1 g of a 4% solution of acetic acid (Aldrich) were supplied. Subsequently, the mixture was transferred to a Hosokawa-Bepex Pharmapaktor L 200/50 G laboratory extruder, operating under the following conditions:
 temperature: 25° C.;
 rotation speed of the screws: 15 rpm;
 applied force: 150 kN.

Pellets were obtained at the exit from the extruder which were dried in the air, then calcined at 550° C. for 5 hours. 300.6 g of silica-alumina ($SiO_2$—$Al_2O_3$) with alumina binder ($Al_2O_3$) in the form of a colourless solid was obtained which was subsequently mechanically granulated and the fraction of granules having dimensions from 0.5 mm to 1.0 mm was used as the catalytic material. Said silica-alumina ($SiO_2$—$Al_2O_3$) with alumina binder ($Al_2O_3$) had a specific BET surface area, determined as reported above, equal to 252 $m^2/g$ and pore modal diameter, determined as reported above, equal to 3 nm.

Example 12 (Disclosure)

Preparation of a Catalyst Based on Silica-Alumina ($SiO_2$—$Al_2O_3$) Having an Alumina Content ($Al_2O_3$) Equal to 1.8% and Pore Modal Diameter Equal to 36 nm, with Alumina Binder ($Al_2O_3$) (Extruded)

A part of the silica-alumina ($SiO_2$—$Al_2O_3$), prepared in Example 5, was subjected to an extrusion process.

For this purpose, 103.0 g of said silica-alumina ($SiO_2$—$Al_2O_3$) and 57.0 g of pseudoboemite Versal™ V-250 (UOP), as an alumina precursor ($Al_2O_3$), of the binder were introduced into an Erweka AR 402 planetary mixer. The powders were mixed at a rotation speed equal to 80 rpm for 2 hours. Subsequently, keeping the rotation speed equal to 80 rpm in the mixer, 450.0 g of a 4% solution of acetic acid (Aldrich) were supplied. Subsequently, the mixture was transferred to a Hosokawa-Bepex Pharmapaktor L 200/50 G laboratory extruder, operating under the following conditions:

temperature: 25° C.;

rotation speed of the screws: 15 rpm;

applied force: 150 kN.

Pellets were obtained at the exit from the extruder which were dried in the air, then calcined at 550° C. for 5 hours. 98.6 g of silica-alumina ($SiO_2$—$Al_2O_3$) with alumina binder ($Al_2O_3$) in the form of a colourless solid (138 g) was obtained which was subsequently mechanically granulated and the fraction of granules having dimensions from 0.5 mm to 1.0 mm was used as the catalytic material. Said silica-alumina ($SiO_2$—$Al_2O_3$) with alumina binder ($Al_2O_3$) had a specific BET surface area, determined as reported above, equal to 226 $m^2/g$ and pore modal diameter, determined as reported above, equal to 36 nm.

Table 1 shows the different types of catalysts obtained in Examples 1-12.

TABLE 1

| Example | Type | pH | Ageing (hours) | Pore modal diameter (nm) |
|---|---|---|---|---|
| 1 (comparative) | silica-alumina ($SiO_2$—$Al_2O_3$) | 12 | — | 7 |
| 2 (comparative) | silica-alumina ($SiO_2$—$Al_2O_3$) from Example 1, with alumina binder | — | — | 3 |
| 3 (disclosure) | silica-alumina ($SiO_2$—$Al_2O_3$) | 8.5 | — | 14 |
| 4 (disclosure) | silica-alumina ($SiO_2$—$Al_2O_3$) from Example 3, with alumina binder | — | — | 14 |
| 5 (disclosure) | silica-alumina ($SiO_2$—$Al_2O_3$) | 8.5 | 72 | 40 |
| 6 (disclosure) | silica-alumina ($SiO_2$—$Al_2O_3$) from Example 5, with alumina binder | — | — | 37 |
| 7 (disclosure) | silica-alumina ($SiO_2$—$Al_2O_3$) | 8.5 | 72 | 37 |
| 8 (disclosure) | silica-alumina ($SiO_2$—$Al_2O_3$) from Example 7, with alumina binder | — | — | 36 |
| 9 (disclosure) | silica-alumina ($SiO_2$—$Al_2O_3$) | 8.5 | — | 100 |
| 10 (disclosure) | silica-alumina ($SiO_2$—$Al_2O_3$) from Example 9, with alumina binder | 8.5 | — | 100 |
| 11 (comparative) | silica-alumina ($SiO_2$—$Al_2O_3$) from Example 1, with alumina binder (extruded) | — | — | 3 |
| 12 (disclosure) | silica-alumina ($SiO_2$—$Al_2O_3$) from Example 5, with alumina binder (extruded) | — | — | 36 |

From the comparison between Example 1 (comparative), Example 3 (disclosure), Example 5 (disclosure), Example 7 (disclosure) and Example 9 (disclosure), it can be seen that through suitable expedients, such as the pH variation in one phase of the silica-alumina synthesis ($SiO_2$—$Al_2O_3$), an increase in ageing in another phase of the synthesis or, finally, by the use of compounds having the function of pore forming or templating such as, for example, compounds containing heteroatoms such as phosphorus (P) (as reported, for example, by Wen Wen and others, "Effect of sol aging time on the anti-reflective properties of silica coatings templated with phosphoric acid", *Results in Physics* (2016), pages 1012-1014, https://doi.org/10.1016/j.rinp2016.11.028) it is possible to obtain a catalyst having a pore modal diameter in accordance with the present disclosure. It should be noted that, for the purpose of the present disclosure, said expedients are to be intended as examples and not limitations of the same: the pore modal diameter in accordance with the present disclosure could also be obtained by means of other methods.

From the comparison between Example 3 (disclosure) and Example 4 (disclosure), it can be seen that the pore modal diameter, after binding, is in accordance with the present disclosure.

From the comparison between Example 7 (disclosure) and Example 8 (disclosure), it can be seen that the pore modal diameter, after binding and extrusion, is in accordance with the present disclosure.

From the comparison between Example 5 (disclosure), Example 6 (disclosure) and Example 12 (disclosure), it can be seen that the pore modal diameter, after binding (Example 6) and extrusion (Example 12), is in accordance with the present disclosure.

Finally, from the comparison between Example 1 (comparative), Example 2 (comparative) and Example 11 (comparative), starting from a catalyst having a pore modal diameter outside the range of the present disclosure it can be seen that the pore modal diameter, after binding (Example 2) and extrusion (Example 11), are not in accordance with the present disclosure.

Examples 13-18

Catalytic Tests

The catalytic materials obtained in Examples 1-12 were used in the catalytic dehydration test of a mixture of butenols obtained by catalytic dehydration of 1,3-butanediol operating as described in Examples 8-15 of the international patent application WO 2016/135609 reported above.

The mixtures of butenols obtained at the exit of the reactor were distilled obtaining an aqueous solution of isomeric butenols having the composition reported in Table 2.

TABLE 2

| | Composition (%) |
|---|---|
| 2-buten-1-ol | 24 |
| 3-buten-2-ol | 40 |
| 3-buten-1-ol | 0.4 |
| water | 35 |

The aqueous solution of butenols reported in Table 2, diluted in water as reported in Table 3, was subjected to catalytic dehydration operating as follows.

The reactor in which said catalytic dehydration reaction was carried out is a tubular reactor with fixed bed made of AISI 316L steel, 350 mm long and with an internal diameter of 9.65 mm. Inside the reactor, along the axis thereof, there was a well with an external diameter equal to 3 mm which housed the thermocouple for temperature regulation. The reactor was placed in an oven with electric heating which allowed to reach the temperature selected for the aforesaid reaction.

The catalyst charge, equal to 3 g, was inserted in the aforesaid reactor between two layers of inert material (corundum), the catalytic bed was held in place by means of a sintered steel septum placed on the bottom of the down-flow reactor.

The feeding was carried out from the top of the reactor, above the area filled with inert material which acted as an evaporator and allowed the reactants to reach the reaction temperature before coming into contact with the catalyst.

The liquid reagents were fed through a metering pump of the type used in "High Performance Liquid Chromatography" (HPLC). The gases were supplied through the "Thermal Mass Flow-meter" (TMF). Downstream of the reactor, the products obtained were cooled in a heat exchanger and the condensed liquid was collected in glass bottles by means of a series of timed valves. The uncondensed gases were instead sent to a volumetric wet gas meter, in order to measure the volume of gases produced. A small portion of the gases were sampled in an on-line gas chromatograph (GC) for analysis. The on-line gas analysis was carried out using an Agilent HP7890 gas chromatograph (GC) with a 50 m long HP—Al/S column with 0.53 mm diameter, 15 micron of film, the carrier used was helium with a flow equal to 30 cm/s, the detector was with flame. The analysis of the gases was carried out using an external standard with calibration curves for the single known components.

The characterization of the collected liquids was carried out by gas chromatographic analysis using an Agilent HP6890 gas chromatograph (GC) equipped with a "Split/Splitless" injector on a 25 m high Quadrex 007 FFAP column with 0.32 mm diameter, 1 micron of film, the carrier used was helium with a speed equal to 50 cm/s, the detector was with flame. The determination was carried out by means of an internal standard with calibration curves for the single known components.

The catalytic material used in the form of granules having dimensions between 0.5 mm and 1 mm and in an amount equal to 3 g, was prepared as described above in Examples 2 (comparative), 4 (disclosure), 6 (disclosure), 8 (disclosure), 10 (disclosure), 11 (comparative) and 12 (disclosure).

Table 3 shows: the catalyst used (Catalyst); the temperature to which the catalytic dehydration is carried out [T (° C.)]; the contact time [τ (s)] calculated as the ratio of the volume of catalytic material loaded to feeding volumetric rate; the dilution implemented, that is the molar ratio of water:butenols being fed, obtained by adding suitable amounts of water to the butenol mixture [Dilution (mol/mol)]; productivity to 1,3-butadiene ($g_{1,3\text{-}BDE}/g_{CAT}$) defined as the amount of 1,3-butadiene produced expressed in grams, compared to the amount of catalytic material used expressed in grams, on a single cycle, reached before the conversion drops below 80%.

TABLE 3

| Example | Catalyst | T (° C.) | τ (s) | Dilution (mol/mol) | ($g_{1,3\text{-}BDE}/g_{CAT}$) (grams) |
|---|---|---|---|---|---|
| 13 | Example 2 (comparative) | 300 | 1.2 | 1.8:1 | 100 |
| 14 | Example 4 (disclosure) | 300 | 1.2 | 1.8:1 | 130 |
| 15 | Example 6 (disclosure) | 300 | 1.2 | 1.8:1 | 185 |
| 16 | Example 10 (disclosure) | 300 | 1.2 | 1.8:1 | 240 |
| 17 | Example 11 (comparative) | 300 | 1.2 | 1.8:1 | 70 |
| 18 | Example 12 (disclosure) | 300 | 1.2 | 1.8:1 | 125 |
| 19 | Example 8 (disclosure) | 300 | 1.2 | 4.3:1 | 163 |

The data reported in Table 3 show the following:

from the comparison between Example 13 (comparative) and Example 14 (disclosure) it can be seen that a silica-alumina ($SiO_2$—$Al_2O_3$) having a pore modal diameter higher than 10 nm in accordance with the present disclosure, allows obtaining a higher productivity ($g_{1,3\text{-}BDE}/g_{CAT}$);

from the comparison between Example 13 (comparative), Example 14 (disclosure) and Example 15 (disclosure), it can be seen that a silica-alumina ($SiO_2$—$Al_2O_3$) having a pore modal diameter in accordance with the present disclosure, obtained thanks to the increase of ageing of the gel in the synthesis phase, allows obtaining a high productivity ($g_{1,3\text{-}BDE}/g_{CAT}$);

from the comparison between Example 13 (comparative) and Example 16 (disclosure), it can be seen that a silica-alumina ($SiO_2$—$Al_2O_3$) having a pore modal diameter in accordance with the present disclosure, obtained thanks to the use of $NaH_2PO_4 \cdot H_2O$ in the synthesis phase, allows obtaining a high productivity ($g_{1,3\text{-}BDE}/g_{CAT}$);

from the comparison between Example 17 (comparative), Example 18 (disclosure) and Example 19 (disclosure), it can be seen that a silica-alumina ($SiO_2$—$Al_2O_3$) having a pore modal diameter in accordance with the present disclosure, obtained by extrusion, allows obtaining a high productivity ($g_{1,3\text{-}BDE}/g_{CAT}$).

Example 19

Life Tests of the Catalyst of Example 8

The catalyst obtained as described in Example 8 was subjected to a life tests consisting of a series of reaction cycles and subsequent regeneration if the conversion of the reactants had dropped below 80%.

The regeneration was carried out in the following modalities: the catalyst was loaded into a tubular reactor with fixed bed AISI 316L, 350 mm long and with an internal diameter of 9.65 mm and was brought to a temperature of 450° C. in nitrogen flow (GHSV=1500 $h^{-1}$) for 1 hour in order to remove therefrom all the volatile organic compounds present. Subsequently, air gradually began to be sent to said reactor progressively increasing the concentration thereof until the complete supply of air in the range of 4 hours. The regeneration was carried on for another 24 hours at the end of which the catalyst was cooled to the reaction temperature in nitrogen ($N_2$) and used in the subsequent reaction cycle.

Table 4 shows, for some of the reaction cycles carried out [No. Cycle (React./Reg.)]; the reaction time ("Time on Stream"—T.o.S.) (hours), that is, the time during which the catalyst has been in contact with the feeding stream under the process conditions before the conversion drops below 80%; the contact time [$\tau$ (s)] calculated as the ratio of the catalytic material loaded to feeding volumetric rate; the dilution used, that is the molar ratio water:butenols being supplied, obtained by adding suitable amounts of water to the mixture of butenols [Dilution (mol/mol)]; productivity at 1,3-butadiene ($g_{1,3\text{-}BDE}/g_{CAT}$) defined as the amount of 1,3-butadiene produced expressed in grams, compared to the amount of catalytic material used expressed in grams, on a single cycle, reached before the conversion drops below 80%.

TABLE 4

| No. Cycle (React./Reg.) | T.o.S. (hours) | T (° C.) | $\tau$ (s) | Dilution (mol/mol) | ($g_{1,3\text{-}BDE}/g_{CAT}$) (grams) |
| --- | --- | --- | --- | --- | --- |
| 3 | 240 | 300 | 1.2 | 4.3:1 | 163 |
|   |     | 300 |     |       |     |
| 9 | 933 | 300 | 1.2 | 4.3:1 | 155 |
| 14 | 1536 | 300 | 1.2 | 4.3:1 | 160 |
| 17 | 1897 | 300 | 1.2 | 4.3:1 | 144 |
| 38 | 3953 | 300 | 1.2 | 4.3:1 | 163 |

From the data reported in Table 4 it can be seen that silica-alumina ($SiO_2$—$Al_2O_3$) of Example 8, having a pore modal diameter in accordance with the present disclosure, allows obtaining a good productivity ($g_{1,3\text{-}BDE}/g_{CAT}$) even after several reaction/regeneration cycles. Furthermore, it should be noted that the catalyst had a total duration greater than 4000 hours, it reached 39 reaction cycles undergoing 38 regenerations while maintaining, however, an average productivity, per reaction cycle as described above, higher than 140 grams ($g_{1,3\text{-}BDE}/g_{CAT}$) without ever showing signs of decay.

The invention claimed is:

1. A process for producing a diene, comprising dehydrating at least one alkenol in the presence of at least one catalytic material comprising at least one acid catalyst based on silica ($SiO_2$) and alumina ($Al_2O_3$), said catalyst having an alumina content ($Al_2O_3$) lower than or equal to 12% by weight, with respect to the catalyst total weight, said alumina content being referred to the catalyst total weight without binder, and a pore modal diameter between 9 nm and 170 nm.

2. The process according to claim 1, wherein said alkenol is selected from 3-buten-2-ol (methyl vinyl carbinol), 3-buten-1-ol (allyl carbinol), 2-buten-1-ol (crotyl alcohol), or mixtures thereof.

3. The process according to claim 1, wherein said alkenol is directly obtained from biosynthetic processes.

4. The process according to claim 1, wherein said alkenol derives from the catalytic dehydration of at least one diol.

5. The process according to claim 4, wherein said diol is bio-1,3-butanediol deriving from the fermentation of sugars deriving from biomass, including scraps, residues, waste deriving from said biomass or from the processing thereof.

6. The process according to claim 1, wherein said acid catalyst based on silica ($SiO_2$) and alumina ($Al_2O_3$) is obtained by incipient wetness impregnation wherein the volume of a solution comprising at least one alumina precursor selected from aluminium alkoxides (such as tri-sec-aluminium butoxide), soluble aluminium salts (such as aluminium sulphate), aluminates (such as sodium aluminate), in a suitable concentration, is equal to or slightly lower than the pore volume of a solid support (for example, silica).

7. The process according to claim 1, wherein said catalytic material comprising at least one acid catalyst based on silica ($SiO_2$) and alumina ($Al_2O_3$) is obtained by a process comprising:
  preparing an aqueous solution or an aqueous suspension of alumina ($Al_2O_3$) or of at least one precursor thereof selected from aluminium alkoxides, soluble aluminium salts, and aluminates;
  adding to said aqueous solution or aqueous suspension of alumina ($Al_2O_3$) or of at least one precursor thereof, an aqueous solution or an aqueous suspension of silica ($SiO_2$) or of at least one precursor thereof selected from silicic acids and alkali metal silicates;
  recovering a solid by precipitation or gelation, and optionally subjecting said solid to at least one of:
    ion exchange with at least one compound capable of exchanging ions with the surface of said solid that is selected from aqueous solutions of salts containing ammonium ions;
    binding with at least one silica precursor ($SiO_2$) selected from colloidal silicas, silica alkoxides; or at least one alumina precursor ($Al_2O_3$) selected from boehmite and pseudoboehmite;
    forming by extrusion, spherulization, tableting, or granulation;
  optionally subjecting said solid to thermal treatment and/ or calcination before or after one aforesaid ion exchange, binding, or forming.

8. The process according to claim 7, wherein said catalytic material comprising at least one acid catalyst based on silica ($SiO_2$) and alumina ($Al_2O_3$), obtained after binding and/or forming, has a pore modal diameter between 9 nm and 170 nm.

9. The process according to claim 1, wherein said acid catalyst based on silica ($SiO_2$) and alumina ($Al_2O_3$) has a specific surface area between 40 $m^2/g$ and 800 $m^2/g$.

10. The process according to claim 1, wherein said catalytic material comprises at least one acid catalyst based on silica ($SiO_2$) and alumina ($Al_2O_3$) and at least one binder selected from alumina ($Al_2O_3$), silica ($SiO_2$), zirconium oxide, titanium oxide.

11. The process according to claim 10, wherein said catalytic material comprising at least one acid catalyst based on silica ($SiO_2$) and alumina ($Al_2O_3$) and at least one binder selected from alumina ($Al_2O_3$) or silica ($SiO_2$), and/or subjected to forming, has a specific surface area between 25 $m^2/g$ and 700 $m^2/g$.

12. The process according to claim 1, wherein said process for producing a diene is carried out with a diluent selected from: inert gases such as nitrogen ($N_2$), argon (Ar); or from compounds having a boiling temperature higher than or equal to 50° C. and a melting temperature lower than or equal to 40° C., that are, preferably, in the liquid state at ambient temperature (25° C.) and at ambient pressure (1 atm), such as water, tetrahydrofuran, cyclohexane, benzene; preferably nitrogen ($N_2$), water, more preferably water.

13. The process according to claim 1, wherein said process for producing a diene is carried out:

in case the diluent is selected from inert gases, at a molar ratio of diluent to alkenol/s greater than 0.3:

in case the diluent is selected from compounds having a boiling temperature higher than or equal to 50° C. and a melting temperature lower than or equal to 40° C., that are preferably, in the liquid state at ambient temperature (25° C.) and at ambient pressure (1 atm), at a molar ratio of diluent to alkenol/s between 0.01 and 100.

14. The process according to claim 1, wherein said process for producing a diene is carried out:

at a temperature between 150° C. and 500° C.; and/or at a pressure between 0.05 bara and 50 bara (bara=absolute bars); and/or operating at a contact time (τ), calculated as the ratio of the catalytic material loaded to feeding volumetric rate, between 0.01 seconds and 10 seconds.

15. The process according to claim 1, wherein said catalytic material comprising at least one acid catalyst based on silica ($SiO_2$) and alumina ($Al_2O_3$), is pre-treated at the temperature to which said process for producing a diene is carried out, that is at a temperature between 150° C. and 500° C., in the presence of at least one diluent.

16. The process according to claim 4, wherein the at least one diol is a butanediol.

17. The process according to claim 16, wherein the butanediol is 1,3-butanediol or bio-1,3-butanediol derived from sugar fermentation.

18. The process according to claim 17, wherein the bio-1,3-butanediol is bio-1,3-butanediol derived from the fermentation of guayule, including scraps, residues, waste derived from said guayule or from the processing thereof.

19. The process according to claim 1, wherein said catalytic material comprising at least one acid catalyst based on silica ($SiO_2$) and alumina ($Al_2O_3$) is obtained by a process comprising:

preparing an aqueous solution or an aqueous suspension of alumina ($Al_2O_3$) or of at least one precursor thereof selected from tri-sec-aluminium butoxide, aluminium sulphate, and sodium aluminate;

adding to said aqueous solution or aqueous suspension of alumina ($Al_2O_3$) or of at least one precursor thereof, an aqueous solution or an aqueous suspension of silica ($SiO_2$) or of at least one precursor thereof selected from orthosilicic acid and sodium silicate;

recovering the solid obtained by precipitation or gelation, and optionally subjecting said solid to at least one of:

ion exchange with at least one compound capable of exchanging ions with the surface of the obtained solid that is selected from aqueous solutions containing ammonium acetate, ammonium nitrate, or ammonium sulphate;

binding with at least one silica precursor ($SiO_2$) selected from Ludox® TMA"-Sigma-Aldrich, tetra-ethyl-orthosilicate; or of at least one alumina precursor ($Al_2O_3$) selected from boehmite and VersalTM V-250-UOP; and forming by extrusion, spherulization, tableting, or granulation;

optionally subjecting said solid to thermal treatment and/or calcination before or after one of the aforesaid ion exchange, binding, or forming.

20. The process according to claim 2, wherein said diene is 1,3-butadiene; the pore modal diameter is between 14 nm and 100 nm; and catalyst productivity, defined as the weight of 1,3-butadiene produced divided by the weight of catalyst in a single cycle before the conversion drops to below 80% ($g_{1,3\text{-}BDE}/g_{CAT}$), is greater than or equal to 130.

* * * * *